(12) United States Patent
Palanivel et al.

(10) Patent No.: US 12,177,758 B2
(45) Date of Patent: Dec. 24, 2024

(54) SYSTEMS AND METHODS FOR IDENTIFYING BLOCKAGES OF EMERGENCY EXISTS IN A BUILDING

(71) Applicant: Honeywell International Inc., Charlotte, NC (US)

(72) Inventors: Rajkumar Palanivel, Eden Prairie, MN (US); Amit Kulkarni, Plymouth, MN (US); Douglas Beaudet, Orono, MN (US); Manjuprakash Rama Rao, Bangalore (IN); Atul Laxman Katole, Bangalore (IN); Aditya Narendrakumar Vora, Ahmedabad (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 23 days.

(21) Appl. No.: 17/846,640

(22) Filed: Jun. 22, 2022

(65) Prior Publication Data

US 2022/0338303 A1     Oct. 20, 2022

Related U.S. Application Data

(63) Continuation of application No. 16/567,045, filed on Sep. 11, 2019, now Pat. No. 11,388,775.

(51) Int. Cl.
| | |
|---|---|
| *H04W 76/50* | (2018.01) |
| *A61B 6/02* | (2006.01) |
| *A62B 3/00* | (2006.01) |
| *G06K 9/00* | (2022.01) |
| *G06V 20/00* | (2022.01) |
| *G06V 20/40* | (2022.01) |
| *G06V 20/52* | (2022.01) |
| *H04W 4/90* | (2018.01) |

(52) U.S. Cl.
CPC ............... *H04W 4/90* (2018.02); *A61B 6/022* (2013.01); *A62B 3/00* (2013.01); *G06V 20/36* (2022.01); *G06V 20/46* (2022.01); *G06V 20/52* (2022.01); *H04W 76/50* (2018.02)

(58) Field of Classification Search
CPC .......... H04W 76/50; H04W 4/90; A62B 3/00; G06K 9/00624; G06V 20/52
USPC ....................................................... 348/143
See application file for complete search history.

(56) References Cited

U.S. PATENT DOCUMENTS

| | | | |
|---|---|---|---|
| 1,652,862 | A | 3/1987 | Verslycken |
| 9,007,459 | B2 | 4/2015 | Meyer |
| 9,683,856 | B2 | 6/2017 | Iyer et al. |
| 9,852,592 | B2 | 12/2017 | McSheffrey |
| 2002/0049728 | A1 | 4/2002 | Kaku |

(Continued)

FOREIGN PATENT DOCUMENTS

DE     19938845 A1     3/2000

*Primary Examiner* — Jeffery A Williams
(74) *Attorney, Agent, or Firm* — Seager, Tufte & Wickhem, LLP (57) ABSTRACT

Methods and systems for monitoring blockages of emergency escape routes and emergency exits of a building include capturing a plurality of images which may correspond to an emergency escape route and/or an emergency exit of a building. The plurality of images may be analyzed to determine when a stationary object is present and at least partially blocking the emergency escape route and/or the emergency exit. If a blockage is detected, a user may be notified of the blockage.

19 Claims, 8 Drawing Sheets

(56) References Cited

U.S. PATENT DOCUMENTS

| | | |
|---|---|---|
| 2002/0125435 A1 | 9/2002 | Cofer et al. |
| 2009/0110239 A1* | 4/2009 | Chen ..................... G06T 15/205 |
| | | 382/103 |
| 2012/0008832 A1* | 1/2012 | Wang ............... G08B 13/19613 |
| | | 382/103 |
| 2012/0154583 A1 | 6/2012 | Lundberg et al. |
| 2012/0287295 A1 | 11/2012 | Oota |
| 2013/0002845 A1 | 1/2013 | Fedorenko et al. |
| 2016/0047663 A1 | 2/2016 | Iyer et al. |
| 2016/0342862 A1* | 11/2016 | Liu ........................ G06T 15/04 |
| 2017/0255824 A1 | 9/2017 | Miller et al. |
| 2019/0385430 A1* | 12/2019 | Criado-Perez ...... G06F 18/2415 |

\* cited by examiner

SYSTEMS AND METHODS FOR IDENTIFYING BLOCKAGES OF EMERGENCY EXISTS IN A BUILDING

This is a continuation of co-pending U.S. patent application Ser. No. 16/567,045, filed Sep. 11, 2019, and entitled "SYSTEMS AND METHODS FOR IDENTIFYING BLOCKAGES OF EMERGENCY EXISTS IN A BUILDING", which is incorporated herein by reference.

TECHNICAL FIELD

The present disclosure relates generally to video surveillance systems, and more particularly to systems and methods for identifying blockages of emergency exists in a building.

BACKGROUND

Many buildings include some sort of security system, often including a video surveillance component that includes one or more video cameras and one or more monitoring console. The cameras are often dispersed throughout a building, and the monitoring console displays video streams associated with the cameras to security personnel. Such systems are often used to monitor, record and detect undesirable activity.

SUMMARY

The present disclosure relates generally to video surveillance systems, and more particularly to systems and methods for identifying blockages of emergency exists in a building. Generally, the video surveillance system may identify a region of interest in a scene that corresponds to an emergency exit and/or an escape route of the building, and use video analytics to identify a blockage within the region of interest. In some cases, the video surveillance system may notify a user of the blockage in real time.

In one example, a method for monitoring blockages of emergency escape routes of a building may include capturing a plurality of images which may correspond to a corresponding one of a plurality of escape route segments along a predefined emergency escape route of a building. The method may further include analyzing the plurality of images to determine when a stationary object is present and may at least partially block at least one of the plurality of escape route segments, and when it is determined that a stationary object is present and may at least partially block at least one of the plurality of escape route segments, the method may include notifying a user of a blockage.

In another example, a system for monitoring for blockages of an emergency exit door of a building may include a stereoscopic video camera which may capture a video stream of the emergency exit door and a surrounding area. A video analytics module may be operatively coupled to the stereoscopic video camera. The video analytics module may be configured to define a region of interest in the video stream adjacent to the emergency exit door, identify in the video stream one or more objects in the region of interest, identify when one or more of the objects in the region of interest are blockage objects, and when a blockage object is identified in the region of interest, the video analytics module may provide a notification to a user.

In another example, a method for notifying a user of a blockage of an emergency exit of a building may include receiving and displaying a notification on a user's mobile device, which may notify the user of a detected blockage of an emergency exit of a building. The method may further include displaying an image of the blockage on the user's mobile device.

The preceding summary is provided to facilitate an understanding of some of the innovative features unique to the present disclosure and is not intended to be a full description. A full appreciation of the disclosure can be gained by taking the entire specification, claims, figures, and abstract as a whole.

BRIEF DESCRIPTION OF THE FIGURES

The disclosure may be more completely understood in consideration of the following description of various examples in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DESCRIPTION

The following description should be read with reference to the drawings, in which like elements in different drawings are numbered in like fashion. The drawings, which are not necessarily to scale, depict examples that are not intended to limit the scope of the disclosure. Although examples are illustrated for the various elements, those skilled in the art will recognize that many of the examples provided have suitable alternatives that may be utilized.

All numbers are herein assumed to be modified by the term "about", unless the content clearly dictates otherwise. The recitation of numerical ranged by endpoints includes all numbers subsumed within that range (e.g., 1 to 5 includes, 1, 1.5, 2, 2.75, 3, 3.8, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

Figure 1:
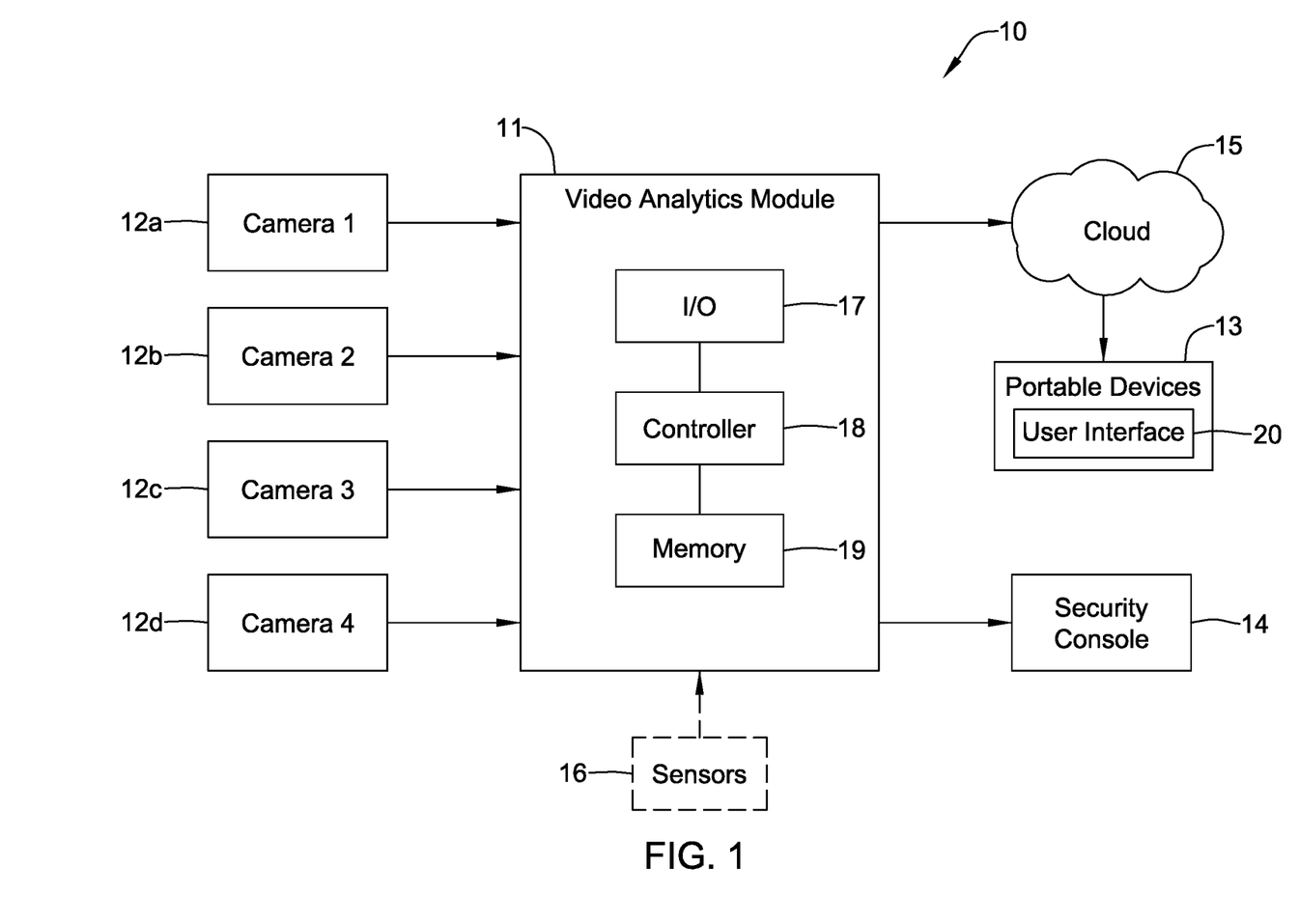
FIG. 1 is a schematic block diagram of an illustrative video surveillance system having a video analytics module in communication with one or more remotely located video surveillance cameras.

FIG. 1 is a schematic view of an illustrative video surveillance system 10 having a video analytics module 11 in communication with one or more remotely located video surveillance cameras 12a, 12b, 12c, and 12d (hereinafter generally referenced as cameras 12). While a total of four video surveillance cameras 12 are shown, it will be appreciated that this is merely illustrative, as there may be any number of video surveillance cameras 12. The video analytics module 11 may be configured to communicate with and/or control one or more components of the video surveillance system 10. For example, the video analytics module 11 may communicate with the one or more components (e.g., cameras 12, security console 14) of the video surveillance system 10 via a wired or wireless link (not shown). Additionally, the video analytics module 11 may communicate over one or more wired or wireless networks that may accommodate remote access and/or control of the video analytics module 11 via another device such as a smart phone, tablet, e-reader, laptop computer, personal computer, or the like. In some cases, the network may be a wireless local area network (LAN). In some cases, the network may be a wide area network or global network (WAN) including, for example, the Internet. In some cases, the wireless local area network may provide a wireless access point and/or a network host device that is separate from the video analytics module 11. In other cases, the wireless local area network may provide a wireless access point and/or a network host device that is part of the video analytics module 11. In some cases, the wireless local area network may include a local domain name server (DNS), but this is not required for all embodiments. In some cases, the wireless local area network may be an ad-hoc wireless network, but this is not required.

In some cases, the video analytics module 11 may be programmed to communicate over the network with an external web service hosted by one or more external web server(s). The video analytics module 11 may be configured to upload selected data via the network to the external web service where it may be collected and stored on the external web server. In some cases, the data may be indicative of the performance of the video surveillance system 10. Additionally, the video analytics module 11 may be configured to receive and/or download selected data, settings and/or services sometimes including software updates from the external web service over the network. The data, settings and/or services may be received automatically from the web service, downloaded periodically in accordance with a control algorithm, and/or downloaded in response to a user request.

Depending on the application and/or where the video surveillance system user is located, remote access and/or control of the video analytics module 11 may be provided over a first network and/or a second network. A variety of remote wireless devices may be used to access and/or control the video analytics module 11 from a remote location (e.g., remote from the video analytics module 11) over the first network and/or the second network including, but not limited to, mobile phones including smart phones, tablet computers, laptop or personal computers, wireless network-enabled key fobs, e-readers, smart watches, and/or the like. In many cases, the remote wireless devices are configured to communicate wirelessly over the first network and/or second network with the video analytics module 11 via one or more wireless communication protocols including, but not limited to, cellular communication, ZigBee, REDLINK™, Bluetooth, WiFi, IrDA, dedicated short range communication (DSRC), EnOcean, and/or any other suitable common or proprietary wireless protocol, as desired.

As discussed above, the video analytics module 11 may be in communication with one or more remotely located video surveillance cameras 12. The cameras 12 may be located along a periphery or scattered throughout an area that is being watched by the cameras 12. The cameras 12 may be controlled via a control panel that may, for example, be part of the video analytics module 11. In some instances, the control panel (not illustrated) may be distinct from the video analytics module 11. It will be appreciated that in some cases, the video analytics module 11 may be located near one or more of the cameras 12. In some cases, the video analytics module 11 may actually be disposed within one or more of the cameras 12. In some cases, the video analytics module 11 may be remote from the cameras 12. The video analytics module 11 may operate under the control of one or more programs loaded from a non-transitory computer-readable medium, such as a memory 19. The video surveillance system 10 may include a security console 14, which may be used to display images provided by the cameras 12 to security personnel.

In some cases, the video analytics module 11 may include a controller 18. In some cases, the controller 18 enables or otherwise may provide the functionality of the video analytics module 11. The video analytics module 11 may include the memory 19 for temporarily storing one or more images captured by a video camera (e.g., cameras 12). The memory 19 may also store software that is used to provide the functionality of the video analytics module 11. The memory 19 may be any suitable type of storage device, including, but not limited to, RAM, ROM, EPROM, flash memory, a hard drive, and/or the like.

The video surveillance system 10 may include one or more sensors 16, which may be remotely located from the video analytics module 11, as shown in FIG. 1. In some cases, the video surveillance system 10 may not include the sensors 16 (as indicated by the dashed lines). The one or more sensors 16 may be positioned adjacent to a region of interest, such as region of interest 31 shown in FIGS. 2 and 3. The one or more sensors 16 may include sensors such as, but not limited to, a pressure mat, a radar sensor, a motion sensor, a door position sensor, a depth sensor, and/or the like. The one or more sensors 16 may be configured to provide real-time data relative to, for example, a pressure sensed within the region of interest to the video analytics module 11. The video analytics module 11 may be configured to use the data received from the one or more sensors 16 and the received video stream to confirm that one or more objects are blocking the region of interest (e.g., an emergency exit door and/or an emergency escape route).

The video analytics module 11 may include or be in communication with a user interface (not shown) including a display and/or a data input device such as a keyboard, a keypad, a joystick, a touch pad, and the like, but this is not required. In some cases, the video analytics module 11 may additionally or alternatively include a remote user interface that facilitates a user's interactions with the video analytics module 11. For example, a user interface 20 may be provided by a number of portable devices 13, such as for example, but not limited to, remote internet devices, including a smart phone, a tablet computer, a laptop computer, or a desktop computer. In some cases, the user interface 20 may communicate with the video analytics module 11 via a router such as, for example, a Wi-Fi or Internet router. In some cases, the user interface 20 may communicate with the video analytics module 11 via a cloud 15.

The video analytics module 11 may further include one or more inputs (e.g., an I/O 17) for receiving signals from a video camera (e.g., cameras 12) and/or receiving commands or other instructions from a remote location. The video analytics module 11 also includes one or more outputs (e.g., the I/O 17) for providing processed images to the portable devices 13 via the cloud 15 and/or to the security console 14. The controller 18 (e.g., a microprocessor, microcontroller, etc.), may be operatively coupled to the memory 19 and the I/O 17. As noted with respect to FIG. 1, the video analytics module 11 may be configured to receive signals from one or more cameras (such as the cameras 12a, 12b, 12c, and 12d, as shown in FIG. 1) that is/are positioned in different spaces within an area. In some cases, the video analytics module 11 may configured to receive a signal from the cameras 12 located throughout an area, via the one or more inputs (e.g., I/O 17). In some cases, the I/O 17 may be a wireless receiver or a wireless transceiver. The cameras 12, as shown in FIG. 1, may include closed circuit television (CCTV) hardware, such as security cameras, networked video recorders, panel controllers, and/or any other suitable camera.

The video analytics module 11 may receive one or more images from the cameras 12 and may analyze the images in order to identify any blockages within a space of a building, such as, for example, along an emergency escape route, an emergency exit door, and/or the like. While discussed with respect to processing live or substantially live video feeds, it will be appreciated that stored images such as playing back video feeds, or even video clips, may be similarly analyzed. In some cases, at least some of the cameras 12 may be stereoscopic video cameras which may provide one or more stereoscopic images to the video analytics module 11. Such stereoscopic images add depth of field relative to monoscopic images. The video analytics module 11 may use this added depth of field information to, for example, help identify a region of interest around an emergency exit door, identify how far a blockage is away from an exit door, movement toward/away from the camera, etc.

Figure 4:
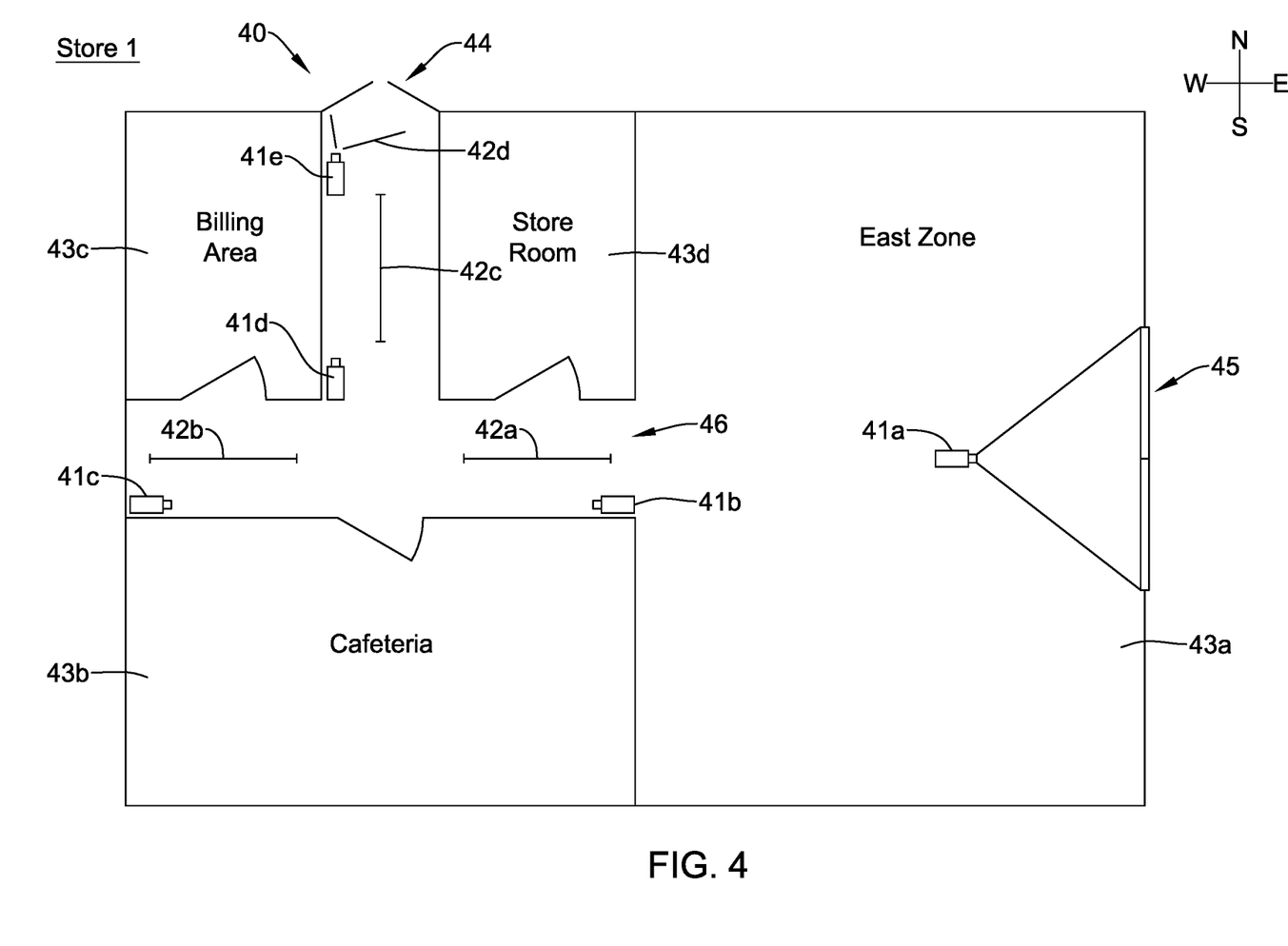
FIG. 4 shows an illustrative building floorplan with a defined emergency escape route leading to an emergency exit door.

As will be discussed, the video analytics module 11 may play a part in analyzing images and/or live video streams in order to detect stationary objects that may be blocking an emergency escape route or an emergency exit door. The emergency escape route may include a plurality of escape route segments, such as shown in FIG. 4 (e.g., 42a, 42b, 42c, 42d). In some examples, the video analytics module 11 may continually update an image captured by one or more of the cameras 12 to look for a stationary object that may be at least partially blocking at least one of the plurality of escape route segments.

In some cases, a reference image may be stored, and continuous image comparison and analysis of the images received from the cameras 12 may be performed by the video analytics module 11. When a difference is detected between the current captured image and the reference image, an object may be detected. In other cases, rather than storing a reference image, the video analytics module 11 may be trained to identify objects in the captured images, often by shape of the object, size of the object, movement of the object and/or other object characteristics. In either cases, the video analytics module 11 may be configured to look for a stationary object that may be at least partially blocking at least one of the plurality of escape route segments, within the live video stream.

Figure 3:
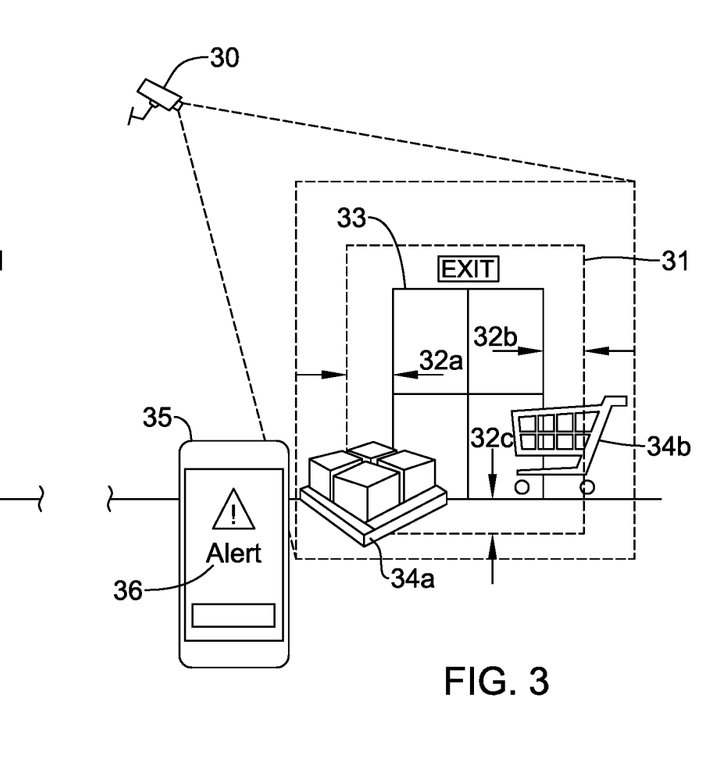
FIG. 3 shows the emergency exit door of FIG. 2 with a blockage in the region of interest, along with a resulting alert notification that is sent to a mobile device of a user.

In some cases, the video analytics module 11 may be configured to classify one or more objects identified within the region of interest into one of two or more object classifications. The two or more object classifications may include a blockage object classification. When one or more objects fall within the blockage object classification, the video analytics module 11 may be configured to provide a notification to a user, as shown in FIG. 3.

In some cases, the video analytics module 11 may include a filter feature, which eliminates reporting filtered objects as a blockage object. For example, one or more filtered object classifications may be defined. When one or more objects fall within one of the filtered object classifications, the video analytics module 11 may "filter out" these objects so as to not be considered blockage objects. In one example, the video analytics module 11 may be configured to recognize an object as a torso of a human, thereby classifying the object into one of the filtered object classification, such as, for example, a human object classification.

Figure 2:
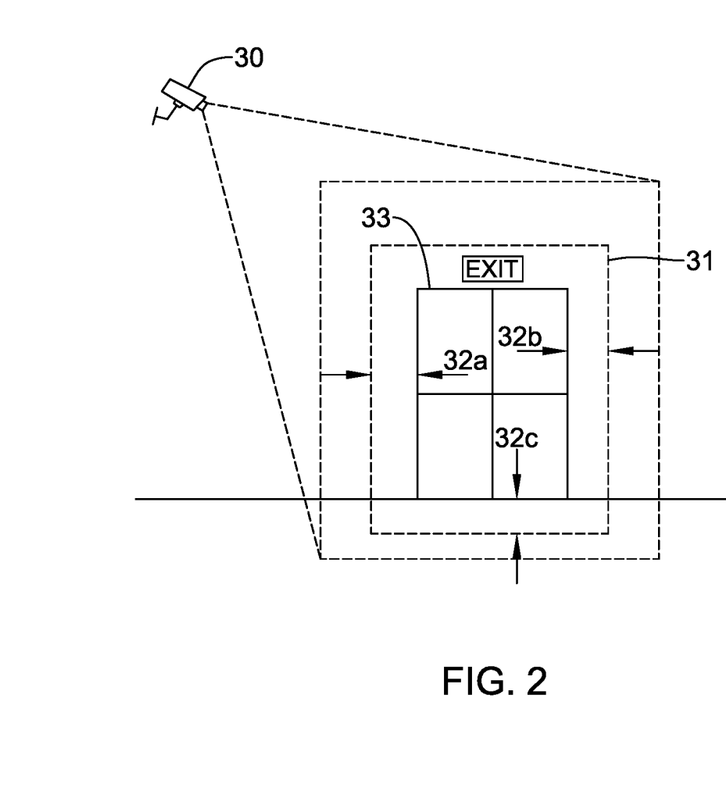
FIG. 2 shows an illustrative exit door location including an emergency exit door, a surveillance camera monitoring the emergency exit door, and a region of interest defined around the emergency exit door.

FIG. 2 shows an illustrative exit door location including an emergency exit door 33, a surveillance camera 30 monitoring the emergency exit door 33, and a region of interest 31 defined around the emergency exit door 33. In some cases, the video analytics module 11 of FIG. 1 may be configured to automatically define the region of interest 31 in the video stream. The region of interest 31 may be located adjacent to the exit door 33, and may span out a distance 32C in front of the exit door 33 and a distance 32A and 32B to each side of the exit door 33 according to a predefined safety code. The video analytics module 11 may be configured to automatically define the region of interest 31 in the video stream, particularly when the surveillance camera 30 is a stereoscopic video camera that adds depth of field information.

The exit door 33 and the region of interest 31 may be monitored by surveillance camera 30. In some cases, the camera 30 may be a stereoscopic camera which may periodically (e.g. 30 Frames Per Second) provide stereoscopic images and/or live feed streams to the video analytics module 11 (see FIG. 1). The camera 30 may be configured to work with an existing camera network (e.g., cameras 12). The stereoscopic images captured by the camera 30 may provide a three-dimensional (3D) stereoscopic view of the region of interest 31, providing a depth of field. In some cases, two separate cameras spaced from one another may be trained on the exit door 33, and together these cameras may provide a depth of field of the region of interest 31. In any event, the video analytics module 11 may analyze the captured video stream and/or images and determine whether a stationary object is in the region of interest 31 defined about the exit door 33. For example, if the region of interest 31 extends ten feet out in front of the exit door 33 and three feet to either side of the exit door, the video analytics module 11 may analyze the captured images and determined if an object is within the region of interest 31.

FIG. 3 shows the emergency exit door 33 of FIG. 2 with a blockage 34A and 34B (e.g., a pallet of boxes 34A and a shopping cart 34B) in the region of interest 31. FIG. 3 also shows a resulting alert notification that is sent to a mobile device 35 of a user. The video analytics module 11 may analyze the image from the camera 30 to determine if the pallet of boxes 34A and the shopping cart 34B fall within the region of interest 31 (as indicated by arrows 32B and 32C, in FIG. 3). When the video analytics module 11 determines that either the pallet of boxes 34A and/or the shopping cart 34B fall within the region of interest 31, the video analytics module 11 may send a notification 36 to a user of a mobile device 35. The notification 36 may include, for example but not limited to, the location of the blockage, the duration of the blockage, the size of the blockage, the direction of the blockage, the material of the blockage, the weight prediction of the blockage, a picture or live video stream of the blockage, and/or the date and time of the occurrence of the blockage. The video analytics module 11 may send the notification 36 to the mobile device 35 via, for example, a cloud network (e.g., cloud 15).

In some cases, as discussed above, one or more sensors (e.g., sensors 16) may be positioned adjacent to the region of interest 31 (not shown). The one or more sensors may include sensors such as, but not limited to, a pressure mat, a radar sensor, a motion sensor, a door position sensor, a depth sensor, and/or the like. In some cases, a pressure mat may detect a weight near the exit door 33 within the region of interest 31. The pressure mat may be operatively coupled to the video analytics module 11, and may send the sensor data to the video analytics module 11. The video analytics module 11 may be configured to use the data received from the one or more sensors and the received video stream to confirm that one or more objects may be blocking the region of interest 31 (e.g., an emergency exit door and/or an emergency escape route).

The video analytics module 11 may determine a duration of time an object has been blocking the region of interest 31. In some cases, the video analytics module 11 may use a duration threshold to determine whether one or more objects are considered to be blocking the region of interest 31. For example, the duration threshold may include, two minutes, five minutes, ten minutes, twenty minutes, thirty minutes, or any other suitable duration of time. When an object, (e.g., the pallet of boxes 34A and/or the shopping cart 34B) is stationary within the region of interest 31 for at least the predetermined duration of time, the notification 36 may be sent to the user of the mobile device 35, alerting the user of a blockage of the exit door 33. When an object (e.g., the pallet of boxes 34A and/or the shopping cart 34B) is placed within the region of interest 31 and then removed before the duration threshold expires, the notification 36 may not be sent to the user of the mobile device 35. This may reduce the number of "false alarms" sent to the user. In some cases, the duration threshold may be programmable. In some cases, a different duration threshold may be assigned to different object classifications. That is, objects that are classified as humans may be assigned a duration threshold that is longer than for objects that are classified as boxes or the like. This is just an example.

In some cases, the video analytics module 11 may be configured to receive one or more input feeds to produce a reference image during installation of the video surveillance system 10. The video analytics module 11 may be configured to store the reference image, and automatically segment the reference image into various components (e.g., a door, a floor, a window, etc.). The video analytics module 11 may automatically identify an escape route or part of an escape route. For example, the video analytics module 11 may be configured to determine that the floor adjacent a door (e.g., exit door 33) may be considered part of an escape route (e.g., part of escape route segments 42, in FIG. 4). The video analytics module 11 may further be configured to determine the width and/or length of the escape route adjacent the door. In some cases, when an object (e.g., the pallet of boxes 34A and/or the shopping cart 34B) is detected in front of the door (e.g., within region of interest 31) the video analytics module 11 may be able to determine an approximate size of the object by comparing the known size of the escape route to the size of the object located in the escape route, and calculate a percentage of the escape route that is blocked. In some cases, the video analytics module 11 may be configured to automatically determine a severity level of the blockage based at least in part on the percentage of the blockage. The severity level may be sent with the notification 36 alerting the user of the mobile device 35 of the severity level of the blockage of the escape route and/or the exit door 33.

In some cases, the video analytics module 11 may be configured to identify signage in the building and use that information to automatically identify an escape route from the building. For example, exit and other signs placed about the building may be recognized by the video analytics module 11, and a semantic analysis of the signage may be used to help automatically identify various escape routes from the building. In some cases, a building model may be provided, along with the locations of the various video cameras of the video surveillance system 10 relative to the building model. The building model may also be used by the video analytics module 11 to automatically identify escape routes from the building. These are just examples.

FIG. 4 shows an illustrative building floorplan 40 with a defined emergency escape route 46 leading to an emergency exit door 44. The building floorplan 40 shows a main entrance 45 that opens into an east zone 43a of the building. The building floorplan 40 further shows a cafeteria 43b, a billing area 43c, and a store room 43d. As shown in FIG. 4, the building floorplan 40 shows a defined emergency escape route 46, which may include a plurality of escape route segments 42a, 42b, 42c, and 42d (hereinafter generally referenced as escape route segments 42). At least some of the escape route segments 42 may be monitored by one of a plurality of cameras 41b, 41c, 41d, and 41e. The plurality of cameras 41a, 41b, 41c, 41d, and 41e (hereinafter generally referenced as cameras 41) may be similar to cameras 12 in FIG. 1.

The cameras 41 may monitor the emergency escape route 46, which includes the plurality of escape route segments 42 and the emergency exit door 44. In some cases, the cameras 41 may be stereoscopic cameras which may provide stereoscopic images and/or live feed streams to the video analytics module 11 (see FIG. 1). The video analytics module 11 may analyze the received video streams and/or captured images to determine if a blockage is detected within any of the plurality of escape route segments 42 and/or in front of the emergency exit door 44. When the video analytics module 11 determines that a blockage exists, the video analytics module 11 may send a notification to a user. The notification may be received on a portable device such as, for example, a smart phone, a tablet computer, a laptop computer, or a desktop computer.

In some cases, when an evacuation of a building is underway (e.g. in response to a fire alarm, gas leak, or other emergency situation), people within the building may use the emergency escape route 46 to exit the building through the emergency exit door 44. The cameras 41 may monitor the plurality of escape route segments 42 and the emergency exit door 44, and send the video streams to the video analytics module 11 (see FIG. 1). The video analytics module 11 (see FIG. 1) may be configured to count the number of people exiting the building through the emergency exit door 44 (and/or other doors via other cameras). The video analytics module 11 may have an employee/visitor list stored in the memory 19, and based on the number of employees/visitors expected to be evacuating the building and the counted number of people exiting the building, the video analytics module 11 may send an alert notification to one or more users indicating whether or not all people expected to evacuate the building have exited the building. In some cases, the employee/visitor list may simply be an employee/visitor count. In some cases, the employee/visitor list and/or employee/visitor count may be generated by employee/visitor badge swipes at the entrance(s) of the building.

In some cases, during an evacuation, the video analytics module 11 may receive the video stream from the cameras 41 and may be configured to determine whether or not a particular emergency escape route 46 is overcrowded. In such cases, the video analytics module 11 may send a notification to one or more users indicating emergency escape route 46 is too crowded and that one or more users should use an alternative exit. In some cases, the emergency escape routes 46 may be indicated by signage in the building. The signage may be dynamically changed by the video analytics module 11 to direct people toward emergency escape routes that are not overcrowded but still deemed safe from the condition that cause the evacuation.

Figure 5:
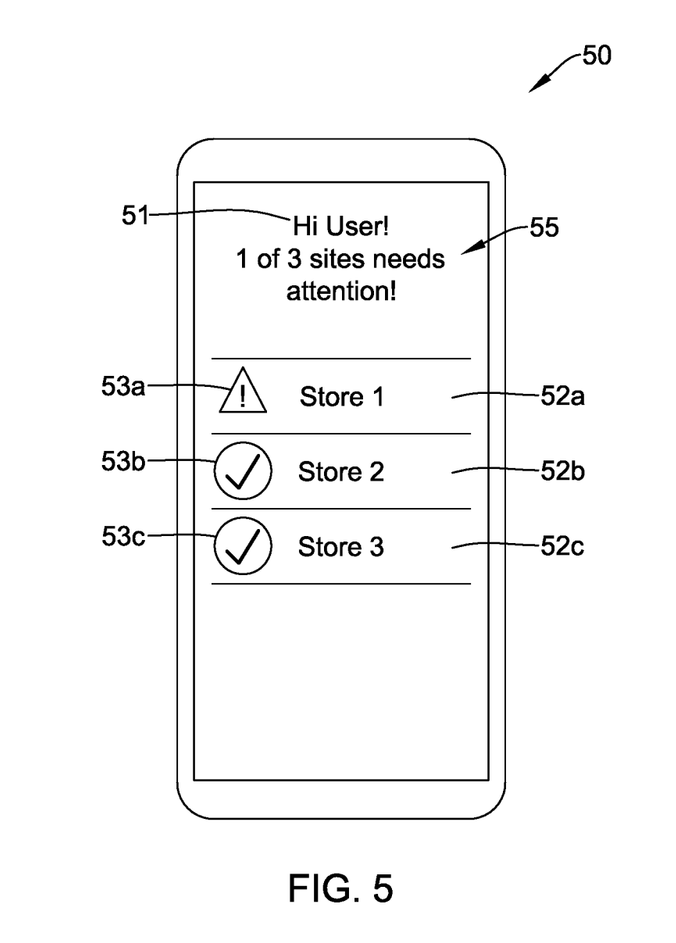
FIG. 5 shows an illustrative screen of a portable device showing a current alert status for various stores.

FIG. 5 shows an illustrative screen 55 of a portable device 50 showing a current alert status for various stores. Some organizations have multiple stores located at different locations (e.g. Walmart, Target, Walgreens, etc.). It may be desirable to monitor safety and other notifications from a user device, such as a mobile device. In the example shown in FIG. 5, the screen 55 may alert a user that one of three Stores may need attention, as indicated by alert notification 51. The screen 55 includes a list of the three sites, Store 1 52a, Store 2 52b, and Store 3 52c. A notification icon may appear next to each store. For example, Store 1 52a may include an icon 53a, Store 2 52b may include an icon 53b, and Store 3 52c may include an icon 53c. In FIG. 5, Store 1 has an alert icon (e.g., the triangle with the exclamation point inside, referenced by 53a). The icons 53b and 53c notify the user that the respective Store (e.g., Store 2 52b and Store 3 52c) does not require attention (e.g., as shown by a circle with a check mark inside, reference by 53b and 53c). In the example shown, a user may select the alert icon 53a for Store 1 to obtain additional information regarding Store 1.

Figure 6:
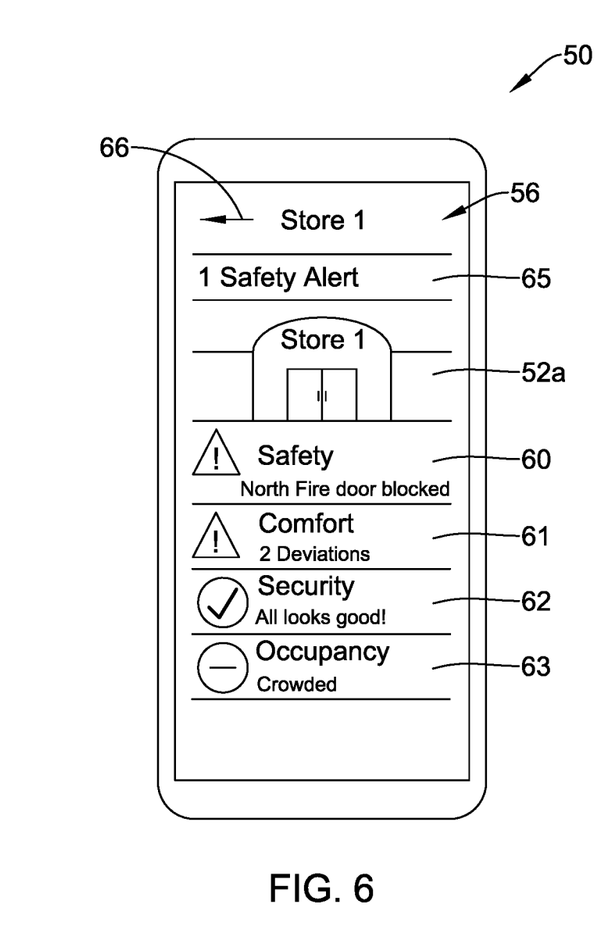
FIG. 6 shows an illustrative screen of a portable device displaying more detailed alert status for Store 1.

FIG. 6 shows additional information regarding Store 1. FIG. 6 shows an image of the Store 1 52a, an alert summary 65, a safety alert section 60, a comfort alert section 61, a security alert section 62, and an occupancy alert section 63. The alert summary 65 notifies the user that there is one safety alert. The safety alert section 60 provides a summary of the current safety alert(s) (e.g. the north fire exit door is blocked). Additionally, the screen 56 in FIG. 6 also alerts the user that there are two comfort alerts in the comfort alert section 61. The security alert section 62 informs a user that there are no security alerts, as indicated by the circle with the check mark inside. The occupancy alert section 63 informs the user that Store 1 52a is crowded and includes a notification icon of a circle with a dash inside.

Figure 7:
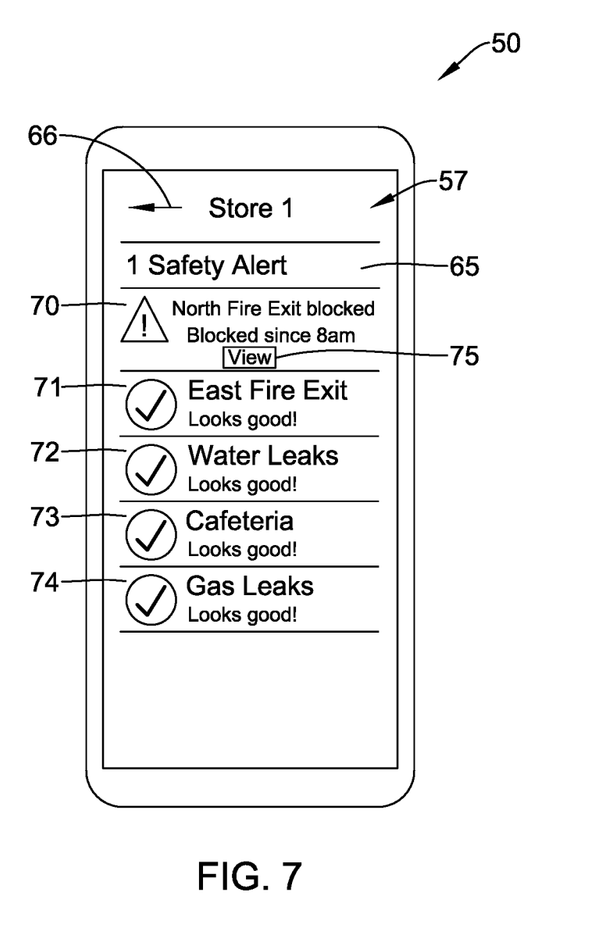
FIG. 7 shows an illustrative screen of a portable device displaying the status for various safety alerts for Store 1.

In the example shown, the user may select the safety alert section 60 of FIG. 6 to gain more information regarding the current safety alerts, an example of which is shown in FIG. 7. The screen 57 of FIG. 7 shows a list of safety conditions monitored within the building. For example, the screen 57 of FIG. 7 shows an alert summary 65, an alert section 70 for the north fire exit, an alert section 71 for the east fire exit, an alert section 72 for water leaks, an alert section 73 for the cafeteria, and an alert section 74 for gas leaks. Alerts 71, 72, 73, and 74 all indicate that the respective safety conditions are not in an alert condition, as indicated by a circle with a check mark inside. The alert section 70 indicates that there is a safety issue at the north fire exit, and further explains the issue (e.g. blocked since 8:00 AM), as indicated by the triangle with the exclamation point inside and alert description. The user may select a view button 75 to view further information, such as an image of the blocked fire exit and/or a link to call local safety personnel at Store 1. An illustrative screen 58 that shows such further information is shown in FIG. 8.

Figure 8:
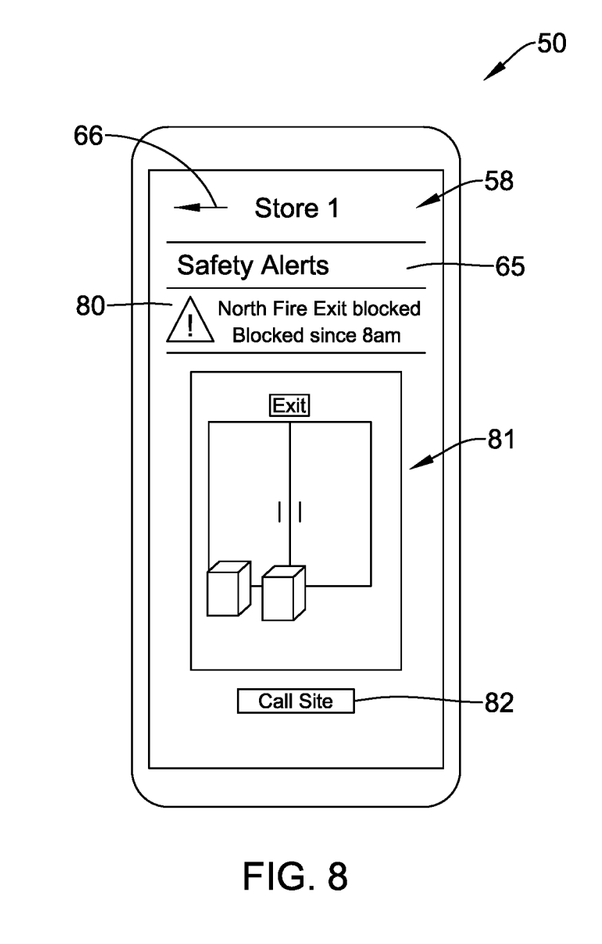
FIG. 8 shows an illustrative screen of a portable device displaying an alert notification corresponding to a detected emergency exist blockage.

As can be seen, the illustrative screen 58 shown in FIG. 8 includes an image 81 of the blockage at the north fire exit. The image 81 may be a still image, a recorded video stream, a live stream. In some cases, any people shown in the image/video 81 may be anonymized by blurring or otherwise hiding the identity of the person before sending the image/video 81 to the mobile device. In some case, a link 82 may be provided for contacting personnel of the building responsible for mitigating the blockage. When the blockage has been cleared, the user may be notified that the blockage has been removed and the alert notification may be removed. As shown in FIGS. 6, 7, 8, and 9, some of the screens (e.g., screens 55, 56, 57, 58, and 59) may include a back arrow 66. The back arrow 66 may allow a user to navigate to the previous screen. By continuing to utilize the back arrow 66, the user may return to the main screen 55, such as shown in FIG. 5.

Figure 9:
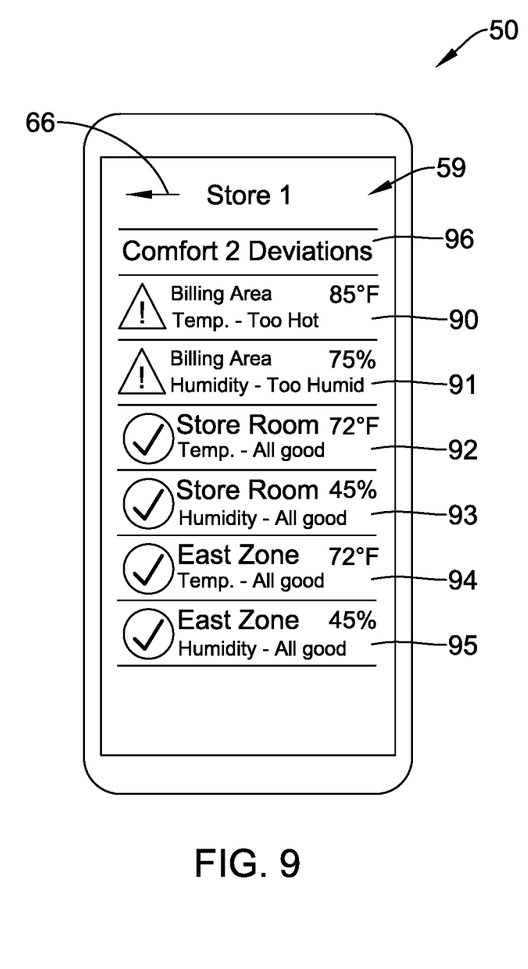
FIG. 9 shows an illustrative screen of a portable device displaying the status for various comfort alerts for Store 1.

In one example, the user may use the back arrow 66 to navigate back to the screen 56 depicted in FIG. 6. The user may then select the comfort alert section 61 (see FIG. 6), which may bring the user to a screen 59 shown in FIG. 9. FIG. 9 shows the status for various comfort alerts for Store 1. At the top of the screen 59, it is indicated that there are two comfort alerts pending. The screen 59 also displays a list of comfort parameters for different rooms within the building. In this example, the list includes a billing area temperature 90, a billing area humidity 91, a store room temperature 92, a store room humidity 93, an east zone temperature 94, and an east zone humidity 95. The comfort parameters 92, 93, 94, and 95 indicate to the user that the parameters in the respective areas are all good, as indicated by a circle with a check mark inside. The comfort parameters 90, 91 for the billing area indicate that the temperature is too hot and the humidity is too high, respectively, as indicated by a triangle with an exclamation point inside and the accompanying alert description. In response, a user may contact personnel responsible for maintaining the HVAC system of Store 1.

Figure 10:
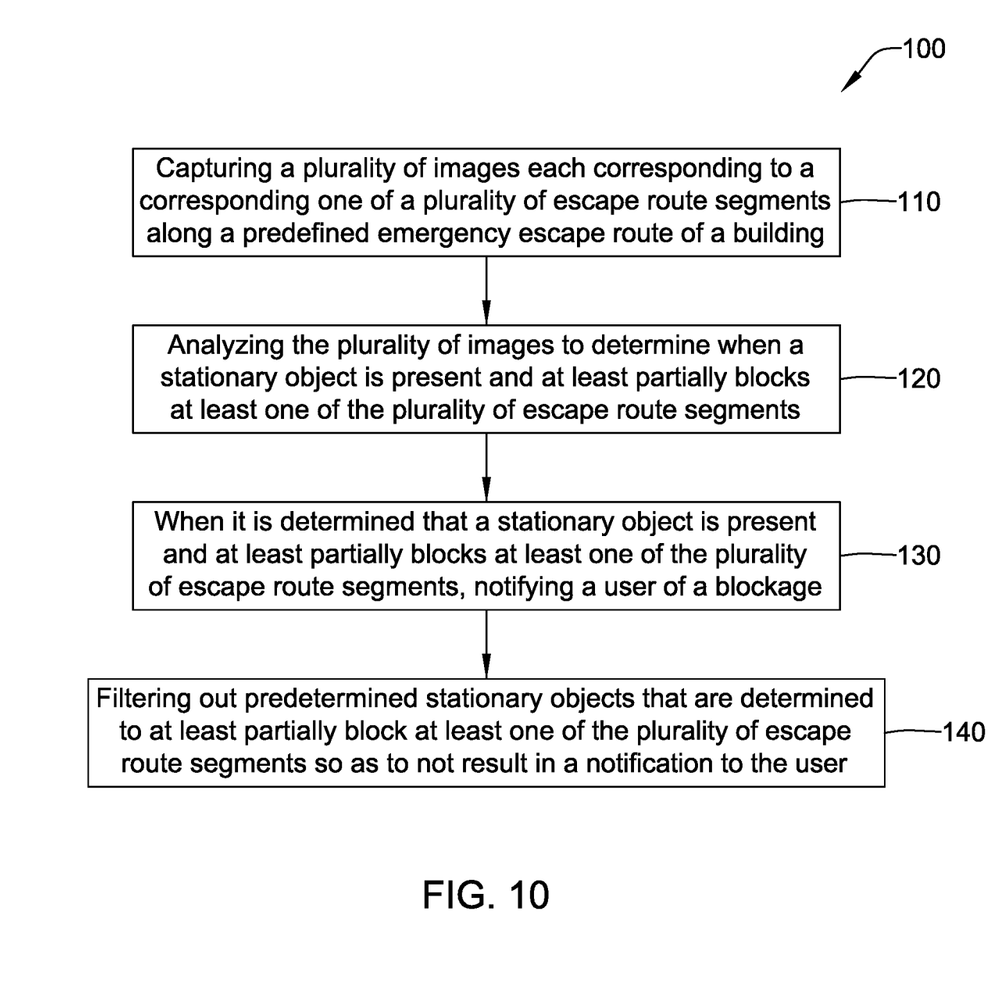
FIG. 10 is a flow diagram showing an illustrative method for monitoring for blockages of emergency escape routes of a building.

FIG. 10 is a flow diagram showing an illustrative method 100 for monitoring for blockages of emergency escape routes of a building. The illustrative method 100 includes capturing a plurality of images each corresponding to a corresponding one of a plurality of escape route segments along a predefined emergency escape route of a building, as referenced at block 110. The plurality of images may be extracted from a plurality of video streams, and the plurality of images may be stereoscopic images. In some cases, the plurality of images may be captured by a plurality of video cameras, and the plurality of video cameras may be automatically identified as corresponding to a corresponding escape route segment of the predefined emergency escape route. The predefined emergency escape route may include an exit door, and an image that corresponds to at least one of the plurality of escape route segments may capture the exit door.

The method 100 may further include analyzing the plurality of images to determine when a stationary object is present, and at least partially blocks at least one of the plurality of escape route segments, as referenced at block 120. Determining when a stationary object is present and at least partially blocks at least one of the plurality of escape route segments may include computing a blockage parameter. The blockage parameter may represent a severity of a blockage of the corresponding escape route segment. The blockage parameter may then be compared to a blockage threshold. When it is determined that a stationary object is present and at least partially blocks at least one of the plurality of escape route segments, the method 100 may include notifying a user of a blockage, as referenced at block 130. The user may be notified by displaying the corresponding image, such as, for example, displaying a live image of the blockage. In some cases, the user may be notified of the blockage when the blockage parameter exceeds the blockage threshold. In some cases, the blockage threshold may correspond to a local safety code.

Figure 11:
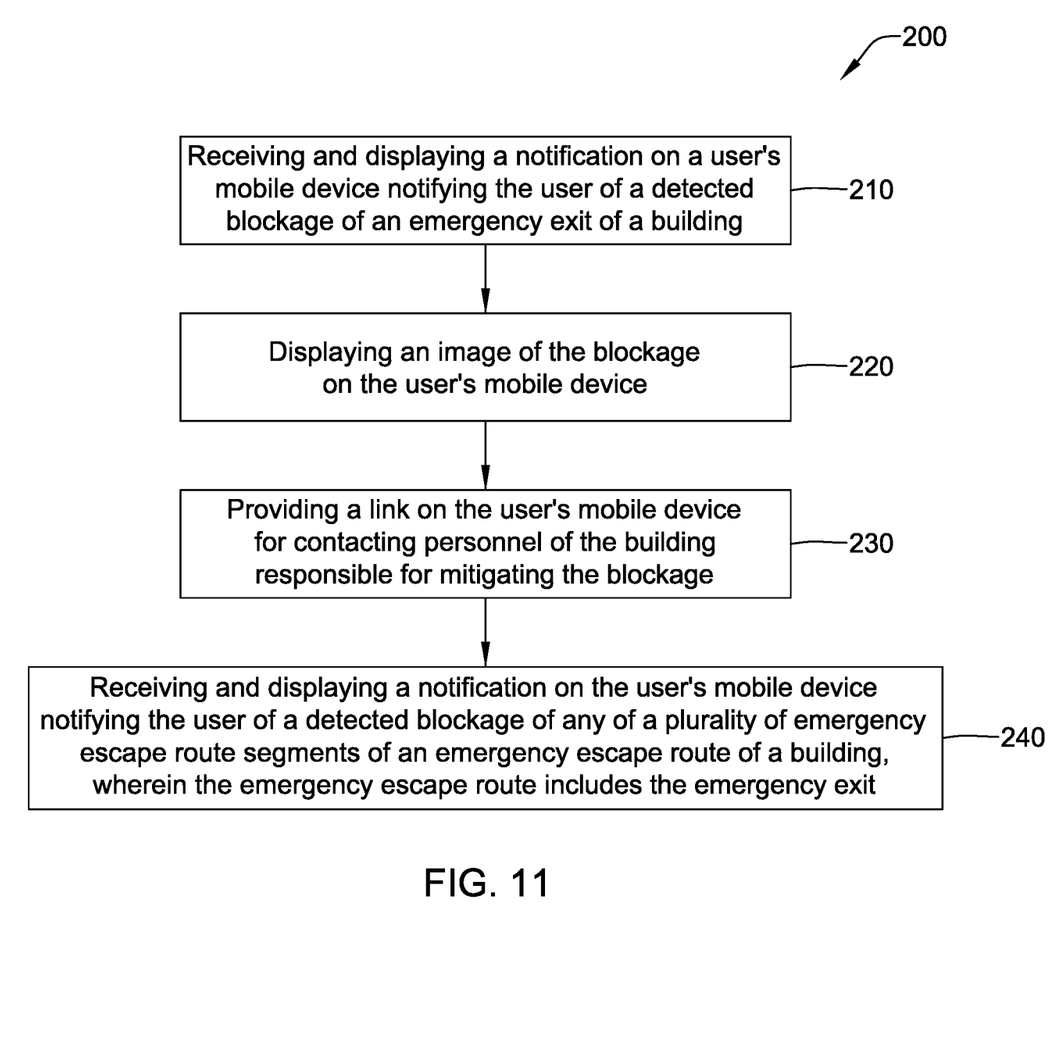
FIG. 11 is a flow diagram showing an illustrative method for notifying a user of a blockage of an emergency exit of a building.

FIG. 11 is a flow diagram showing an illustrative method 200 for notifying a user of a blockage of an emergency exit of a building. The illustrative method 200 includes receiving and displaying a notification on a user's mobile device, and notifying the user of a detected blockage of an emergency exit of a building, as referenced at block 210. The image of the blockage may be displayed on the user's mobile device, as referenced at block 220. A link may be provided on the user's mobile device for contacting personnel of the building responsible for mitigating the blockage, as referenced at block 230. The method 200 may further include receiving and displaying a notification on the user's mobile device, which may notify the user of a detected blockage of any of a plurality of emergency escape route segments of an emergency escape route of a building, wherein the emergency escape route includes the emergency exit.

Having thus described several illustrative embodiments of the present disclosure, those of skill in the art will readily appreciate that yet other embodiments may be made and used within the scope of the claims hereto attached. It will be understood, however, that this disclosure is, in many respects, only illustrative. Changes may be made in details, particularly in matters of shape, size, arrangement of parts, and exclusion and order of steps, without exceeding the scope of the disclosure. The disclosure's scope is, of course, defined in the language in which the appended claims are expressed.

What is claimed is:

1. A method for monitoring for blockages of a passageway in a building, comprising:
    receiving a video stream of at least part of the passageway of the building;
    analyzing the video stream to identify when a stationary object at least partially blocks the passageway of the building;
    determining when the stationary object at least partially blocks the passageway for at least a first period of time;
    classifying the stationary object that at least partially blocks the passageway for at least the first period of time into one of a plurality of object classifications;
    in response to determining that the stationary object at least partially blocks the passageway for at least the first period of time:
        notifying a user of a blockage of the passageway when the stationary object is classified into a first object classification of the plurality of object classifications;
        not notifying or delay notifying the user of the blockage of the passageway when the stationary object is classified into a second object classification of the plurality of object classifications; and
        wherein the first object classification corresponds to inanimate objects and the second object classification corresponds to animate objects.

2. The method of claim 1, comprising:
    notifying the user of the blockage of the passageway when the stationary object is classified into the second object classification of the plurality of object classifications and when the stationary object at least partially blocks the passageway for at least a second period of time, wherein the second period of time is greater than the first period of time.

3. The method of claim 1, wherein identifying when the stationary object at least partially blocks the passageway of the building comprises:
    computing a blockage parameter that represents a severity of a blockage of the passageway by the stationary object;
    comparing the blockage parameter to a blockage threshold; and
    identifying that the stationary object at least partially blocks the passageway of the building when the blockage parameter exceeds the blockage threshold.

4. The method of claim 1, wherein identifying when the stationary object at least partially blocks the passageway of the building comprises:
    identifying a region of interest in a field of view of the video stream that corresponds to at least part of the passageway; and
    identifying that the stationary object at least partially blocks the passageway when the stationary object extends into the region of interest in the field of view of the video stream.

5. The method of claim 4, wherein the region of interest is at least partially manually defined by a user.

6. The method of claim 4, wherein the region of interest is at least partially automatically defined using a building model of the building.

7. A method for monitoring for blockages of passageway in a building, comprising:
    receiving a video stream that has a field of view that includes of at least part of the passageway of the building;
    identifying a region of interest of the field of view of the video stream, wherein the region of interest includes a defined portion of the field of view of the video stream that does not include the entire field of view of the video stream, wherein the region of interest corresponds to at least part of the passageway of the building;

analyzing the video stream to:
- determine when an object extends into the defined region of interest, resulting in a candidate blocking object;
- determine when the candidate blocking object remains stationary for at least a first period of time while extending into the region of interest;

determining that the passageway is at least partially blocked by the candidate blocking object when the candidate blocking object remains stationary for at least the first period of time while extending into the region of interest, resulting in a confirmed blocking object;

determining an object classification of the confirmed blocking object; and notifying a user that the passageway is at least partially blocked by the confirmed blocking object when the confirmed blocking object is classified in a first object classification and not notifying or delaying notifying the user that the passageway is at least partially blocked by the confirmed blocking object when the confirmed blocking object is classified in a second object classification.

8. The method of claim 7, wherein the region of interest is at least partially manually defined by a user.

9. The method of claim 7, wherein the region of interest is at least partially automatically defined using a building model of the building.

10. The method of claim 7, wherein the region of interest within the field of view of the video stream comprises a defined geometric shape in the field of view of the video stream.

11. The method of claim 7, wherein the region of interest within the field of view of the video stream has a depth dimension, and determining when the object extends into the region of interest comprises determining when the object extends into the region of interest in the depth dimension.

12. The method of claim 7, wherein notifying the user that the passageway is at least partially blocked by the confirmed blocking object comprises notifying the user of a location of the confirmed blocking object and a picture or live video of the confirmed blocking object.

13. The method of claim 12, further comprising anonymizing one or more people in the picture or live video of the confirmed blocking object.

14. The method of claim 7, wherein the first object classification corresponds to inanimate objects and the second object classification corresponds to animate objects.

15. A method for monitoring for blockages of a passageway in a building, comprising:
- receiving a video stream of at least part of the passageway of the building;
- analyzing the video stream to identify when a stationary object at least partially blocks the passageway of the building;
- determining when the stationary object at least partially blocks the passageway for a first period of time and when the stationary object at least partially blocks the passageway for a second period of time that is greater than the first period of time;
- classifying the stationary object into one of a plurality of object classifications;
- in response to determining that the stationary object at least partially blocks the passageway for the first period of time:
  - notifying a user of a blockage of the passageway when the stationary object is classified into a first object classification of the plurality of object classifications;
  - not notifying or delay notifying the user of the blockage of the passageway when the stationary object is classified into a second object classification of the plurality of object classifications;
- in response to determining that the stationary object at least partially blocks the passageway for the second period of time:
  - notifying the user of the blockage of the passageway when the stationary object is classified into the second object classification of the plurality of object classifications.

16. The method of claim 15, wherein the first object classification corresponds to inanimate objects and the second object classification corresponds to animate objects.

17. The method of claim 15, wherein identifying when the stationary object at least partially blocks the passageway of the building comprises:
- computing a blockage parameter that represents a severity of a blockage of the passageway by the stationary object;
- comparing the blockage parameter to a blockage threshold; and
- identifying that the stationary object at least partially blocks the passageway of the building when the blockage parameter exceeds the blockage threshold.

18. The method of claim 15, wherein identifying when the stationary object at least partially blocks the passageway of the building comprises:
- identifying a region of interest in a field of view of the video stream that corresponds to at least part of the passageway; and
- identifying that the stationary object at least partially blocks the passageway when the stationary object extends into the region of interest in the field of view of the video stream.

19. The method of claim 18, wherein the region of interest is at least partially manually defined by a user.

\* \* \* \* \*